United States Patent [19]
Chen et al.

[11] Patent Number: 5,904,749
[45] Date of Patent: May 18, 1999

[54] GAS CHROMATOGRAPHIC METHOD

[76] Inventors: Christopher Huk-Shi Chen, 4239 Anworld Place, Mississauga, Ontario, Canada, L4W 2W1; Shinn-Der Chang, 14 Neilson Drive Unit 905, Etobicoke, Ontario, Canada, M9C 1V6; Chengwen Weng; Yuanming Tang, both of P.O. Box 515-25, Chengdu, Sichuan, China; Ingo Bernd Holzhueter, 6 Bimini Crescent, North York, Ontario, Canada, M3N 1R9; Samuel Hugh Hawthorne, 3 Farmington Drive, Brampton, Ontario, Canada, L6W 2V1

[21] Appl. No.: 08/186,900

[22] Filed: Jan. 27, 1994

Related U.S. Application Data

[63] Continuation of application No. 07/990,054, Dec. 14, 1992, abandoned.

[51] Int. Cl.$^6$ .................................................. B01D 15/08
[52] U.S. Cl. .................................................... 95/86; 95/87
[58] Field of Search .............................. 55/267; 95/82, 95/87; 96/101–103; 73/23.25, 23.26, 23.35

[56] References Cited

U.S. PATENT DOCUMENTS

| | | | |
|---|---|---|---|
| 2,377,900 | 6/1945 | Podbielniak | 73/23.26 |
| 3,035,383 | 5/1962 | Sanford et al. | 55/67 |
| 3,043,127 | 7/1962 | Deford et al. | 55/67 X |
| 3,057,183 | 10/1962 | Deford | 55/67 X |
| 3,146,616 | 9/1964 | Loyd | 55/386 X |
| 3,225,521 | 12/1965 | Burow | 55/67 |
| 3,486,299 | 12/1969 | Weiser, Jr. et al. | 55/67 |
| 3,578,757 | 5/1971 | Samuilov . | |
| 3,865,562 | 2/1975 | Ayers et al. | 55/67 |
| 4,469,496 | 9/1984 | Frischmuth et al. | 55/67 X |
| 4,521,225 | 6/1985 | Jenkins et al. | 55/67 X |
| 4,732,581 | 3/1988 | Cheh et al. | 55/67 |
| 4,780,116 | 10/1988 | Cheh et al. | 55/386 |
| 4,923,486 | 5/1990 | Rubey | 55/67 |
| 5,028,243 | 7/1991 | Rubey | 55/386 X |
| 5,135,549 | 8/1992 | Phillips et al. | 55/67 |
| 5,152,176 | 10/1992 | Bryselbout et al. | 55/67 X |
| 5,196,039 | 3/1993 | Phillips et al. | 55/67 |

FOREIGN PATENT DOCUMENTS

| | | |
|---|---|---|
| 0 317 054 | 8/1988 | European Pat. Off. . |
| 2.062.110 | 10/1969 | France . |
| 1 598 449 | 9/1966 | Germany . |
| 1 673 027 | 7/1967 | Germany . |
| 1 951 377 | 10/1969 | Germany . |
| 1204897 | 9/1970 | United Kingdom ................ 55/67 |
| WO 92/13622 | 1/1992 | WIPO . |

OTHER PUBLICATIONS

European Search Report, Application No. 93310043.0, Christopher Huk–Shi Cheh et al.

*Primary Examiner*—Robert Spitzer
*Attorney, Agent, or Firm*—Ridout & Maybee

[57] ABSTRACT

A gas chromatographic method utilizes columns having either ascending or descending temperature profiles to effect separation even under column overloading conditions. A fixed ascending temperature profile column allows for good separation of components of a mixture under conditions of column overloading. A mixture to be separated is chromatographed on at least one such column prior to chromatography on a column maintained with a descending temperature profile. This latter column has surprisingly been found to greatly reduce tailing of less volatile species. The invention also includes a variable temperature descending column chromatography to provide an initial ordering of a large quantity of components prior to chomatography on the fixed ascending temperature profile column, or on the serial fixed ascending and descending temperature profile pair of columns.

9 Claims, 7 Drawing Sheets

GAS CHROMATOGRAPHIC METHOD

This is a continuation of application Ser. No. 07/990,054, filed on Dec. 14, 1992, now abandoned.

The invention is a gas chromatographic method for separating components of a chemical mixture by applying a temperature profile along the length of a column or along the lengths of several columns connected in series.

Previously, gas chromatographic separations have been carried out at a constant temperature or under a temperature program which increases the temperature of the entire column over a specified temperature range at a specified rate. It has long been recognized that temperature programming can provide a gas chromatographic separation which has sharper peaks, i.e. less tailing, than may be achievable with constant temperature gas chromatography. Temperature programming may also allow a larger amount of a mixture to be separated on a column than would be the case under constant temperature conditions.

The separation of chemical mixtures by gas chromatography utilizes the affinity equilibrium properties of the mixture components carried in a mobile gas phase with a stationary phase column packing. Separation of components depends on each component having a different affinity with the stationary phase, and thus, moving through the column at a rate different from the rates for other components. The partition of a mixture component between the mobile and stationary phases is temperature dependent. A temperature for the chromatography which favors the separation of the more volatile components of the mixture may result in long column retention times for the less volatile components. Under such conditions, the volatile components will show relatively sharp elution peaks, i.e., they will come off the column each over a short time period; while the less volatile components will exhibit tailing and may not be fully separated from one another. Conversely, if temperature conditions for the chromatography favor elution of the less volatile components, the volatile components may not have sufficient resident time on the column to effect their separation.

Temperature programming is employed to deal with this problem. By uniformly raising the temperature of the whole column over time the more volatile components may still be separated and the less volatile components are eluted at a rate which improves separation and reduces tailing. Typically, whole column temperature programming is frequently adequate for use in analytical gas chromatographic applications where column overloading is not an issue. However, when a gas chromatography system is required to separate molar quantities of mixtures, the whole column temperature programming technique is unsatisfactory since the load of material for separation applied to the column invariably results in persistent tailing.

Conventionally, preparative gas chromatography involves loading a mixture for separation via a sample loop from which the mixture is loaded onto the column using a carrier gas. Large samples require long sample loops and result in dilution of the mixture as it is loaded onto the column. This dilution further contributes to peak broadening and incomplete separation of components.

The present invention departs from the established temperature programming techniques to provide a gas chromatographic method which enables the achievement of superior separations even of large quantities of mixtures using surprisingly small columns. Rather than increasing the temperature of the entire column over time to effect a gas chromatographic separation, the present method utilizes a constant temperature profile along the length of the column, thereby affecting the rate of elution of each mixture component in each temperature zone. In a column having an ascending temperature profile, the temperature effect causing the more volatile components to move along the column faster than the less volatile components is enhanced when compared with whole column programmed heating. Ascending temperature profile chromatography also allows the column to be overloaded so that a surprisingly large amount of mixture can be processed. In some cases, this overloading of the column results in broadening of the elution of the less volatile components, but it has been found that by coupling an ascending temperature profile column with at least one descending temperature profile column, this broadening or tailing effect is greatly reduced.

A constant descending temperature profile is thought to be unique for a gas chromatography process. This descending temperature mode provides an unexpected enhancement for an overall separation of a mixture initially subjected to a constant ascending temperature profile chromatography.

Accordingly, the present invention provides a gas chromatographic method comprising loading a mixture onto a column maintained at an elution temperature profile wherein the temperature increases along the column length from the inlet to the outlet of the column; flowing the mixture through the column to effect at least a partial separation of the mixture components; and recovering the separated or partially separated components from the outlet of the column.

The invention also includes the two stage gas chromatographic method wherein after the mixture passes through the first column maintained at an ascending temperature profile, the effluent from the first column is flowed through a second column maintained at a temperature profile wherein the temperature decreases along the column length from the inlet to the outlet. Preferably, the temperature profile in the second column is approximately inverse to that of the first column. Separated components of the mixture are recovered from the outlet of the second column.

A further embodiment of the invention which is particularly useful for separating a large quantity of a mixture involves the use of a first column having a variable descending temperature profile over a large temperature range, usually more than 100° C., followed by elution through a second column having an ascending temperature profile maintained over a relatively narrow temperature range, usually of less than 100° C. A third column maintained with a decreasing temperature profile is preferably included to optimize the separation. The variable descending temperature profile column provides an initial rough ordering of mixture components, thereby essentially providing a means for efficiently loading a large quantity of a mixture onto the temperature ascending mode column.

To illustrate the power of the gas chromatography method of the invention, it will be described by way of example as it may be applied to the preparative scale separation of isotopic mixtures of hydrogen. However, the skilled person will appreciate the general applicability of the invention for the analytical and preparative separation of mixtures of compounds by gas chromatography.

Figure 1:
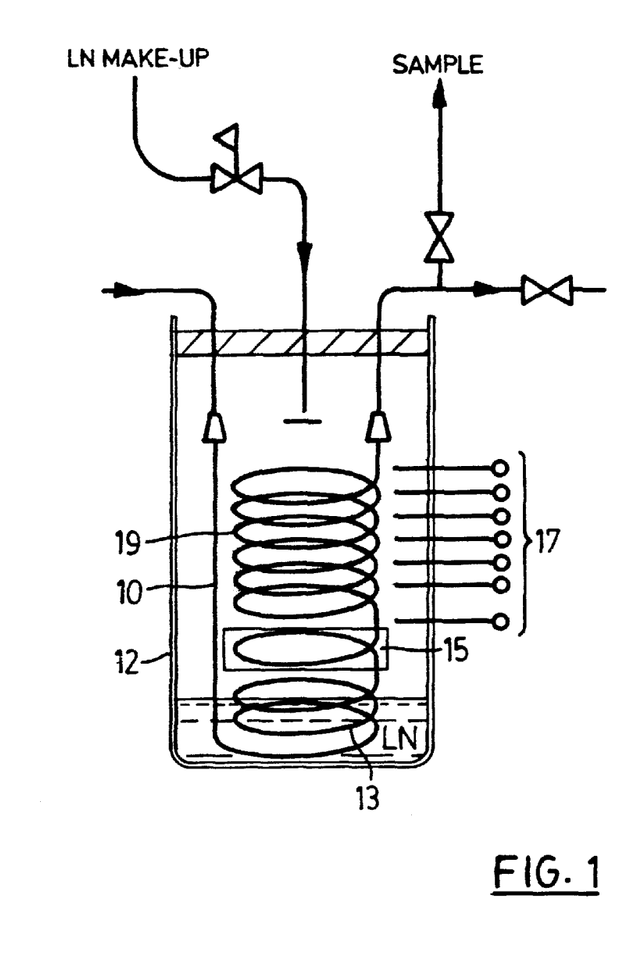
FIG. 1 is a schematic diagram of a column having an ascending temperature profile.

Referring to FIG. 1, a helically coiled chromatography column 10 is positioned within an insulated container 12, such as a vacuum jacketed Dewar container, and liquid nitrogen (LN) is added to the container 12 to a level immersing a sufficient length of the column 10 to cool the influent mixture to less than the desired initial temperature. This inlet precooling portion 13 of the column 10 is preferably packed with a material having low affinity for the components of the mixture, so that the mixture will have a short residence time in this portion 13 of the column 10.

Liquid nitrogen boils under atmospheric pressure at $-196°$ C. A temperature profile is produced and maintained within the container 12 using an insulated electrical heating tape 15 or similar adjustable heating means about the column 10 just above the liquid nitrogen level in the container 12. The temperature profile is sensed using a plurality of temperature sensors 17 positioned vertically within the container 12 adjacent the adsorbent packed portion 19 of the overall column 10.

Figure 2:
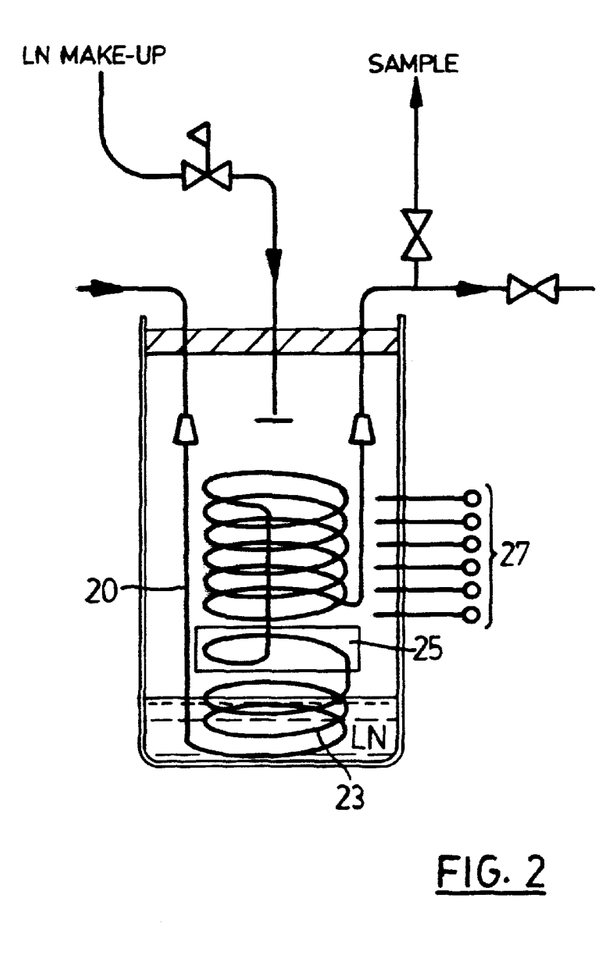
FIG. 2 is a schematic diagram of a column having a descending temperature profile.

Likewise, a temperature descending mode column 20 is shown in FIG. 2, wherein the inlet portion of the column 20 includes a precooler section 23 packed with a material having a low affinity for the components of the mixture followed by the column 20 maintained at a descending temperature profile using an adjustable heating means 25 and temperature sensing means 27 as described for the column 10 of FIG. 1.

Figure 3:
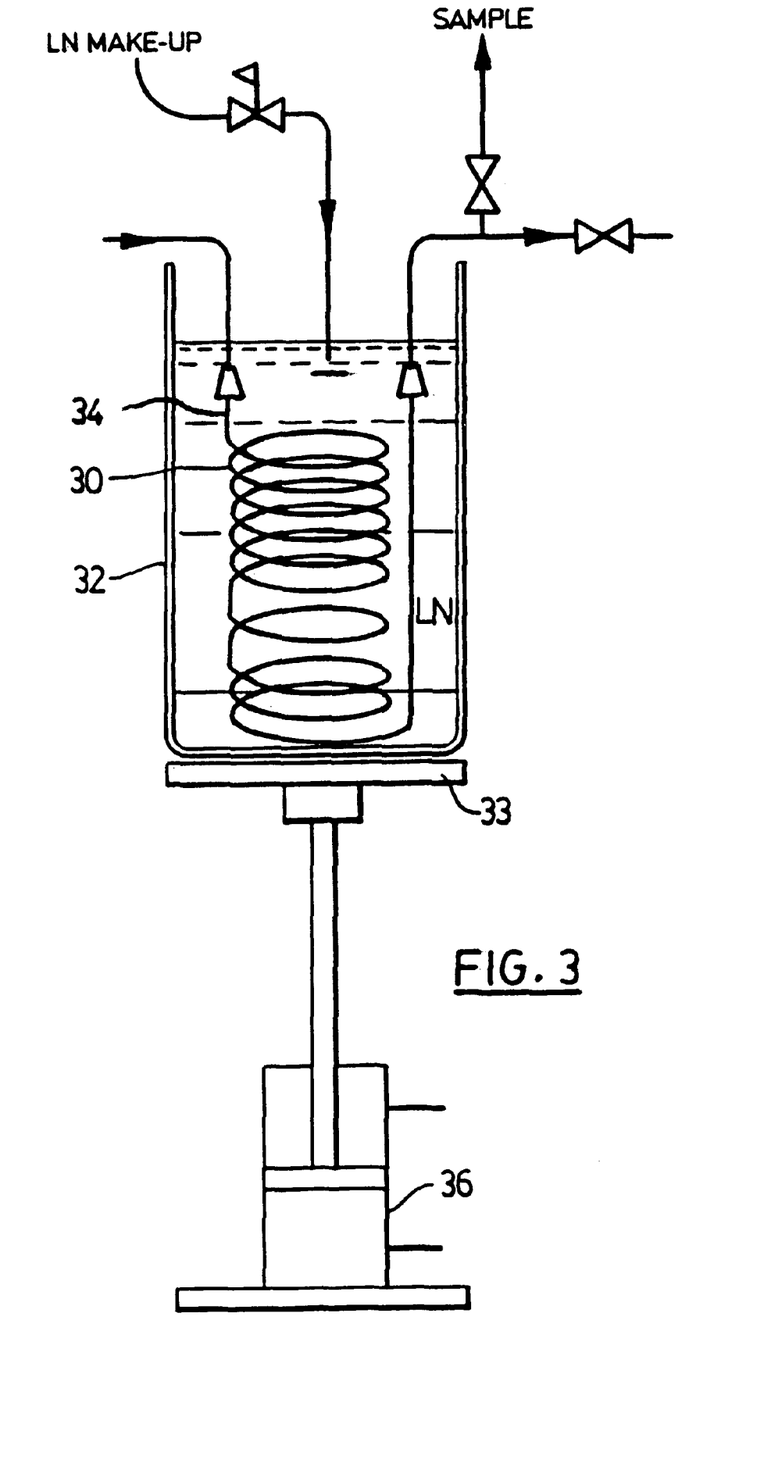
FIG. 3 is a schematic diagram of a column having a variable descending temperature profile.

A third type of column particularly useful in preparative chromatography applications is shown in FIG. 3. A gas chromatography column 30 is immersed in liquid nitrogen in a Dewar or other suitable insulated container 32. The container 32 is located on a vertically retractable platform 33, and as the mixture is eluted, the platform is gradually retracted, for example, by means of a hydraulic piston 36, thereby allowing the column temperature to rise beginning at the inlet end 34. The retraction of the container 32 creates a relatively large temperature difference between those portions of the column 30 which are immersed in liquid nitrogen and those portions which are exposed to the ambient environs. This type of column is most useful as a pre-stage for large amounts of mixture to be fully separated on a fixed ascending temperature profile column or on a fixed ascending temperature profile and fixed descending temperature profile column pair. Preferably, the large volume of mixture to be separated is loaded onto the column 30 by first evacuating the column 30 and using the pressure differential to inject the gaseous mixture into the column 30. This loading technique avoids initial dilution of the mixture with the carrier gas and enables the separation of such similar species as hydrogen isotopes under conditions of extreme column overloading. Thus, in preparative chromatography applications the column 30 allows for a rough ordering of mixture components by volatility prior to their entry into the columns 10 and 20 of FIGS. 1 and 2.

Once loaded onto a column of the invention, the mixture is eluted using a carrier gas. For the chromatographic separation of hydrogen isotopes, helium is the preferred carrier gas. The following examples are illustrative of the invention as it relates to the preparative separation of hydrogen isotopes. The skilled person will appreciate that the invention has equal applicability to analytical gas chromatography, but the following examples are provided to illustrate the power of the invention.

EXAMPLE 1

Figure 4:
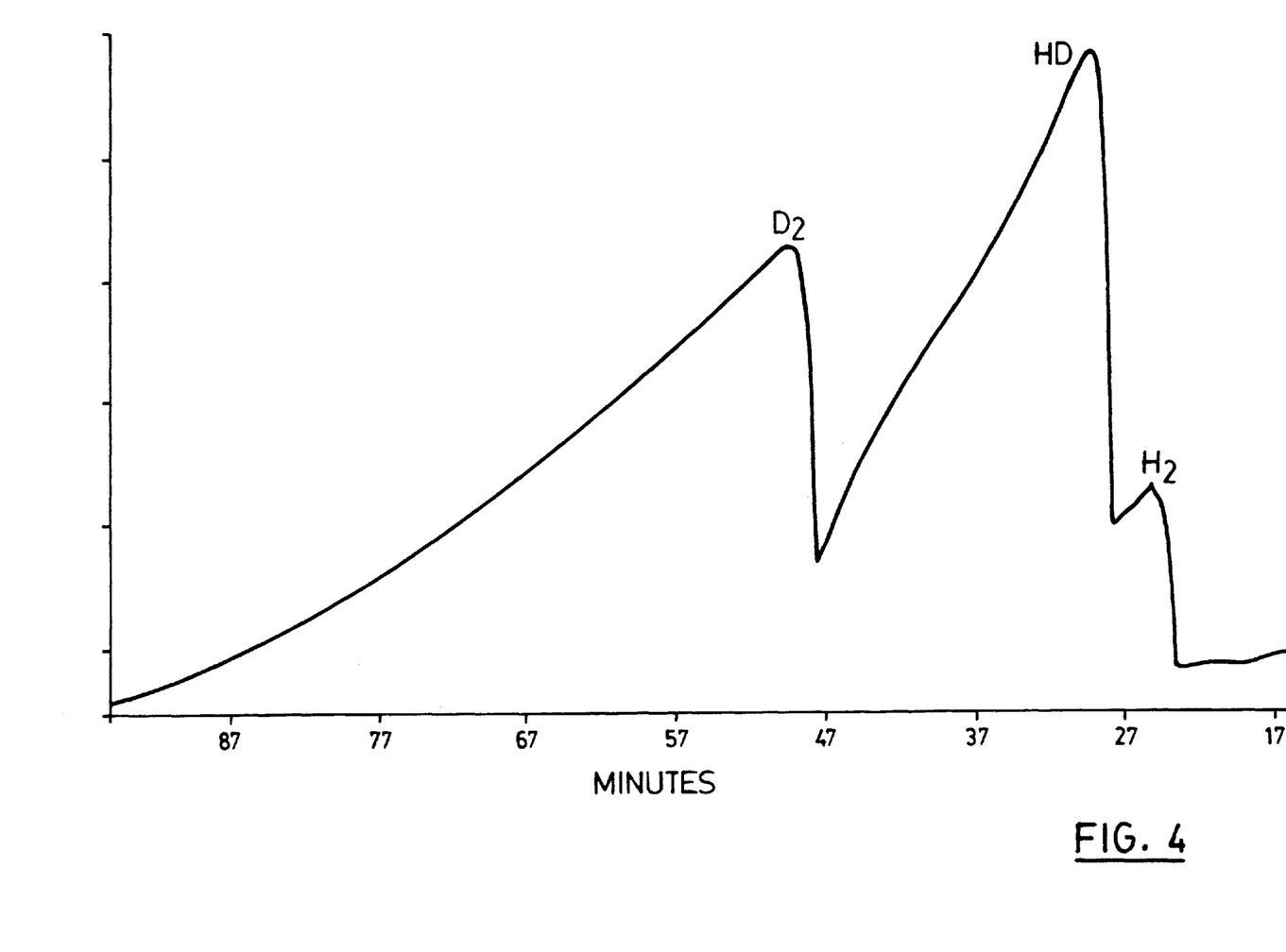
FIGS. 4–8 are chromatograms made in accordance with various embodiments of the invention.

A large sample mixture totalling 6.2 l of $H_2$, HD and $D_2$ (at 0° C., 1 atm.) was vacuum loaded onto a variable temperature descending mode column 30 (FIG. 3) which had a diameter of 12 mm, a length of 4.6 m and was packed with 5A molecular sieves. The column 30 was immersed in liquid nitrogen during loading, and then the column 30 was eluted with helium at a rate of 1.5 l/min. while the liquid nitrogen container was gradually retracted over about a 30 min. period. This variable temperature descending mode column 30 was connected in series with an ascending temperature profile column 10 of 12 mm diameter and 4.9 m in length (FIG. 1). The column 10 was packed with 5A molecular sieves and an ascending temperature profile of $-170°$ C. to $-143°$ C. was maintained along its length. The chromatogram is shown in FIG. 4.

EXAMPLE 2

Figure 5:
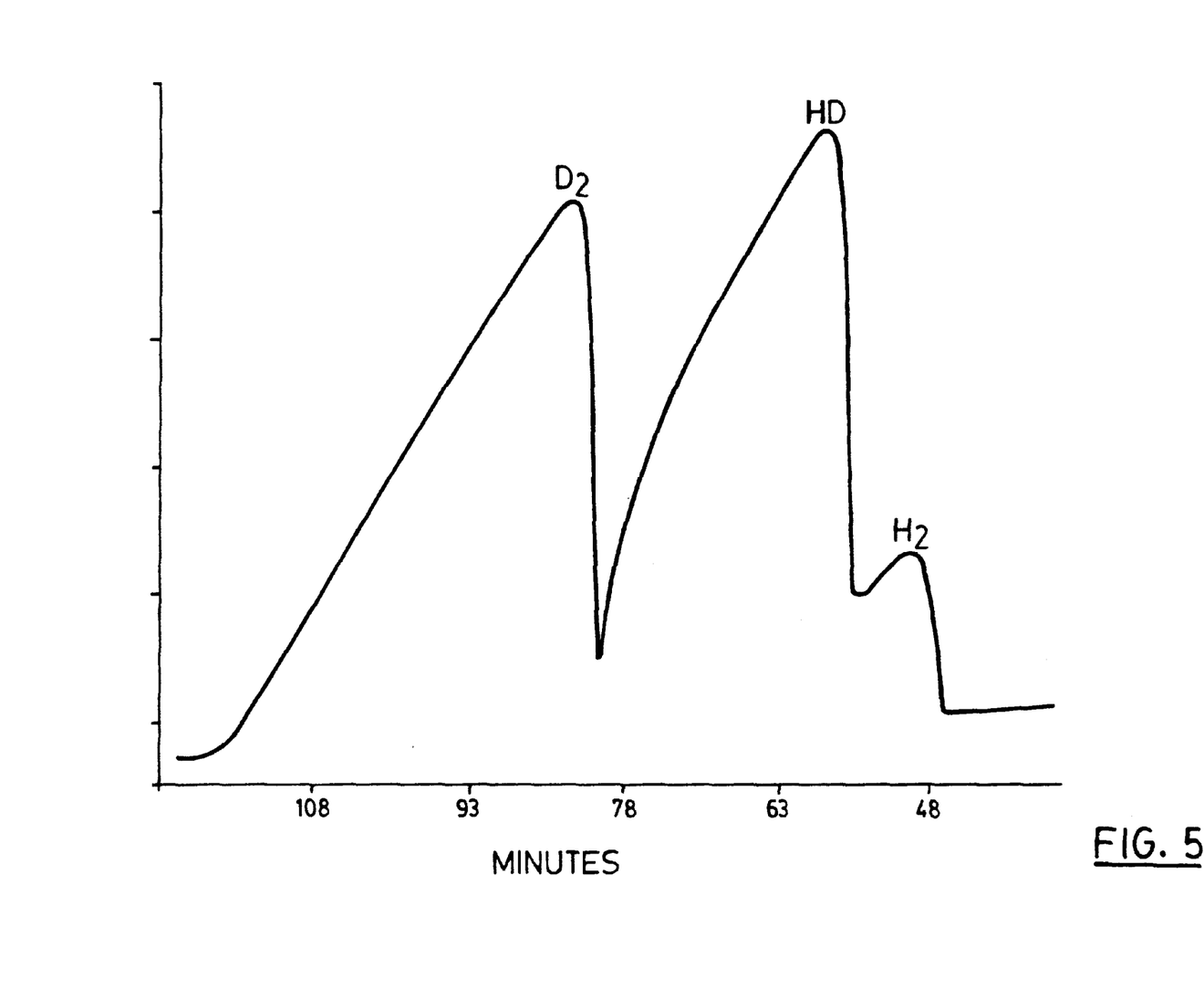

A 5.7 l mixture of $H_2$, HD and $D_2$ (at 0° C., 1 atm.) was vacuum loaded onto a variable temperature descending mode column 30 (FIG. 3) which had a diameter of 12 mm, a length of 4.6 m and was packed with 5A molecular sieves. The column 30 was immersed in liquid nitrogen during loading, and then the column 30 was eluted with helium at a rate of 2.5 l/min. while the liquid nitrogen container was gradually retracted over about a 30 min. period. This variable temperature descending mode column 30 was connected in series with a temperature ascending and a temperature descending column pair. The ascending temperature mode column 10 was as described in Example 1 but having a length of 4.6 m, and the fixed ascending temperature profile was $-170°$ C. to $-138°$ C. The descending temperature profile mode column 20 (FIG. 2) had a diameter of 12 mm and a length of 4.6 m, and the fixed temperature profile was $-145°$ C. to $-155°$ C. The chromatogram is shown in FIG. 5.

EXAMPLE 3

Figure 6:
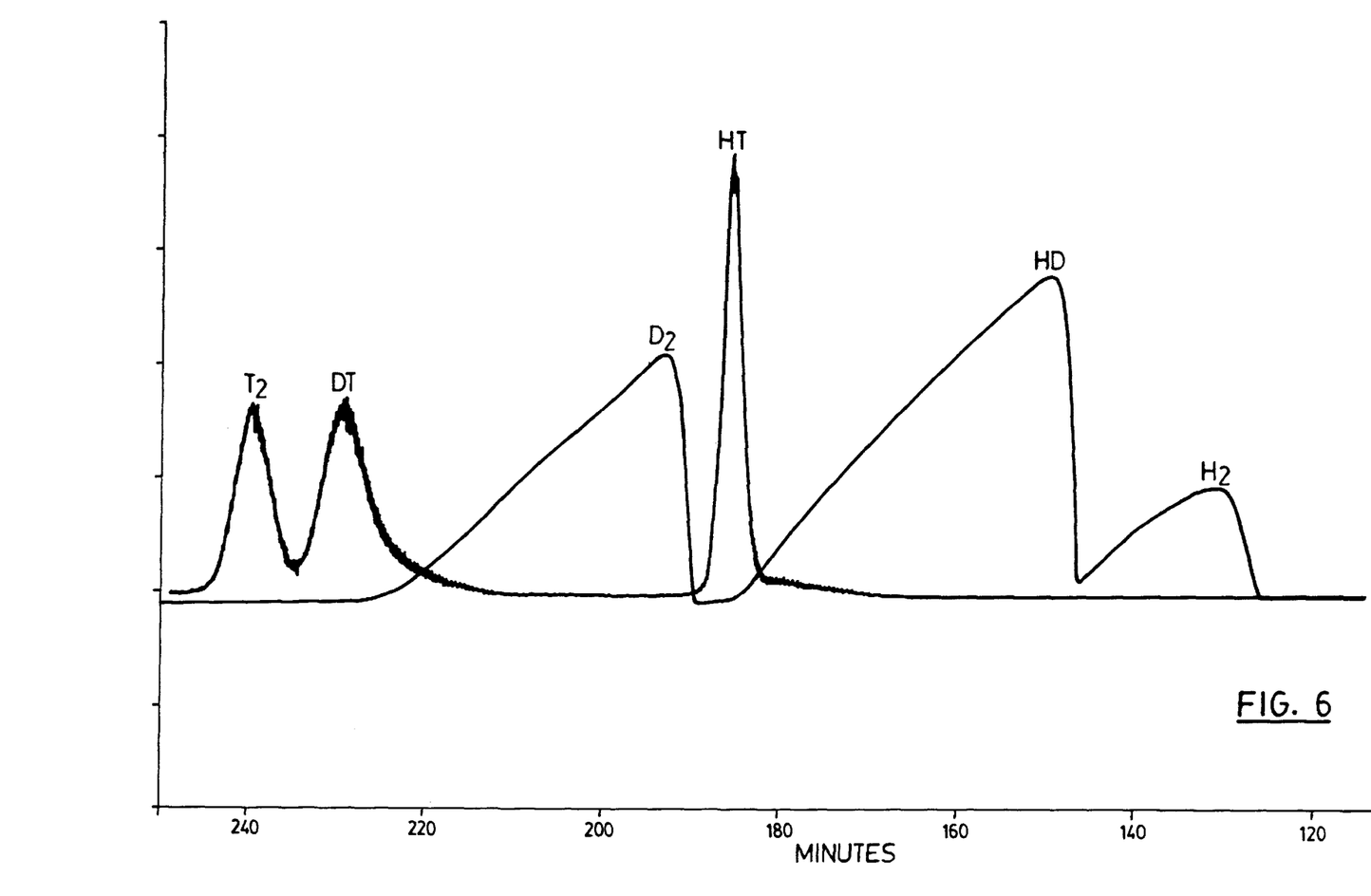

A mixture of 2.1 l $H_2$, HD, HT, $D_2$, DT and $T_2$ (at 0° C., 1 atm.) was vacuum loaded onto a variable temperature descending mode column 30 (FIG. 3) which had a diameter of 12 mm, a length of 4.6 m and was packed with 5A molecular sieves. The column 30 was immersed in liquid nitrogen during loading, and then the column 30 was eluted with helium at a rate of 2.5 l/min. while the liquid nitrogen container was gradually retracted over about a 30 min. period. This variable temperature descending mode column 30 was connected in series with a temperature ascending and descending column pair as described in Example 2, where the fixed ascending temperature profile was $-168°$ C. to $-152°$ C. and the fixed descending temperature profile was $-147°$ C. to $-165°$ C. The chromatogram is shown in FIG. 6.

EXAMPLE 4

Figure 7:
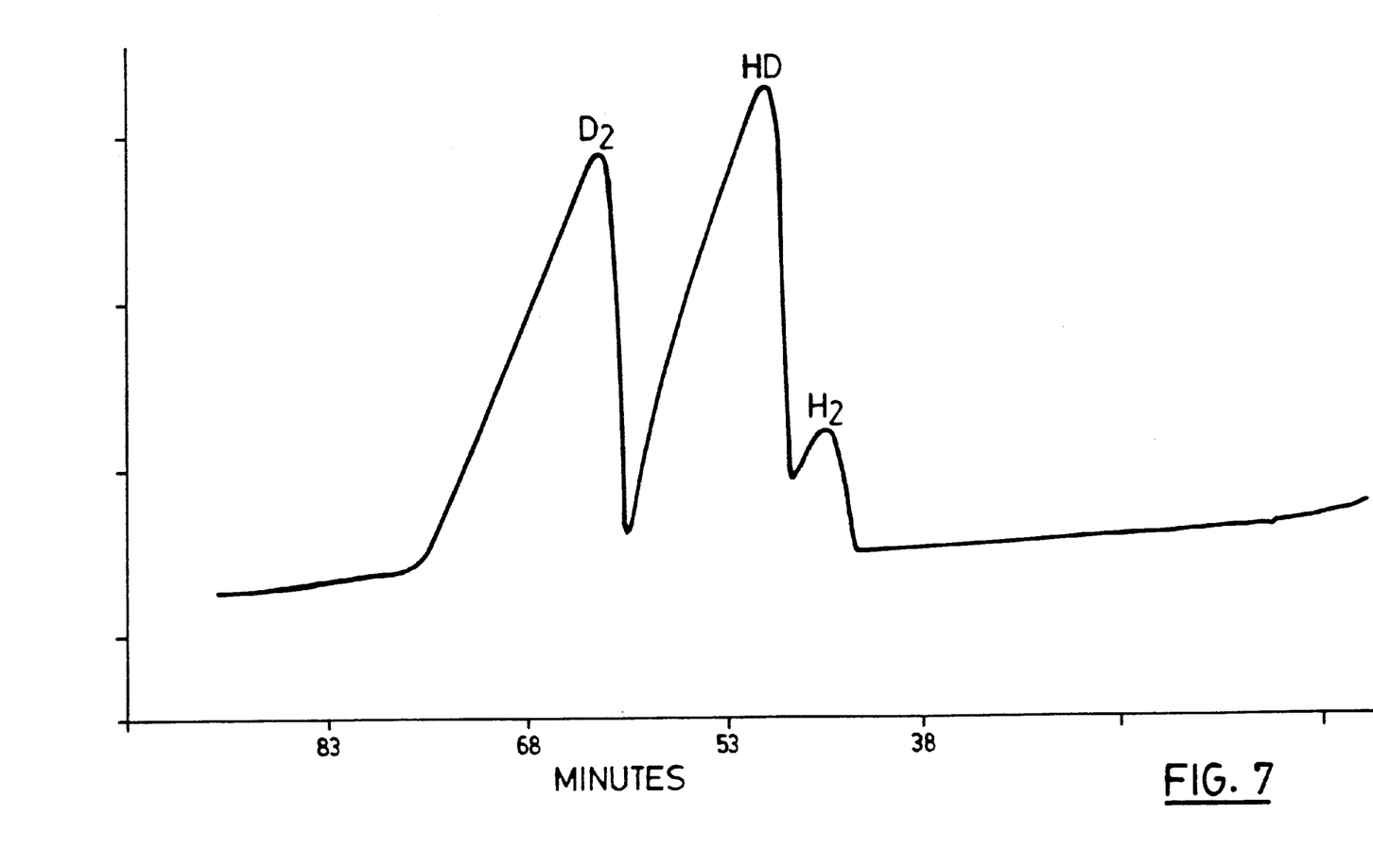

A mixture of $H_2$, HD and $D_2$ having a volume of 1.9 l (at 0° C., 1 atm.) was loaded onto a column 30 using the vacuum feed mode. The column 30 was packed with 5A molecular sieves and had a diameter of 12 mm and a length of 4.6 m. The column 30 was immersed in liquid nitrogen during loading, and then the column 30 was eluted with helium at a rate of 2.5 l/min. while the liquid nitrogen container was gradually retracted over about a 30 min. period. This variable temperature descending mode column 30 was connected in series with a similar sized column 10 packed with 5A molecular sieves but maintained under a fixed ascending temperature profile of −155° C. to −130° C. This column 10 was connected in series to a descending temperature profile column 20 of the same size having a fixed temperature profile of from −130° C. to −157° C., inlet to outlet. The components were fully eluted from the third column 20 in about 75 min. as seen from the chromatogram of FIG. 7.

EXAMPLE 5

On a preparative scale, the process of the invention may be performed continuously in that successive batches of mixtures may be separated pursuant to sequential loadings onto the column system. Thus, a first mixture of $H_2$, HD, HT, $D_2$, DT and $T_2$ of 1.0 l ( (at 0° C., 1 atm.) was loaded onto a column 30 using the vacuum feed mode. The column 30 was packed with 5A molecular sieves and had a diameter of 12 mm and a length of 4.6 m. The column 30 was immersed in liquid nitrogen during loading, and then the column 30 was eluted with helium at a rate of 2.5 l/min. while the liquid nitrogen container was gradually retracted over about a 30 min. period. This variable temperature descending mode column 30 was connected in series with a similar sized column 10 packed with 5A molecular sieves but maintained under an ascending temperature profile of −165° C. to −145° C.

Figure 8:
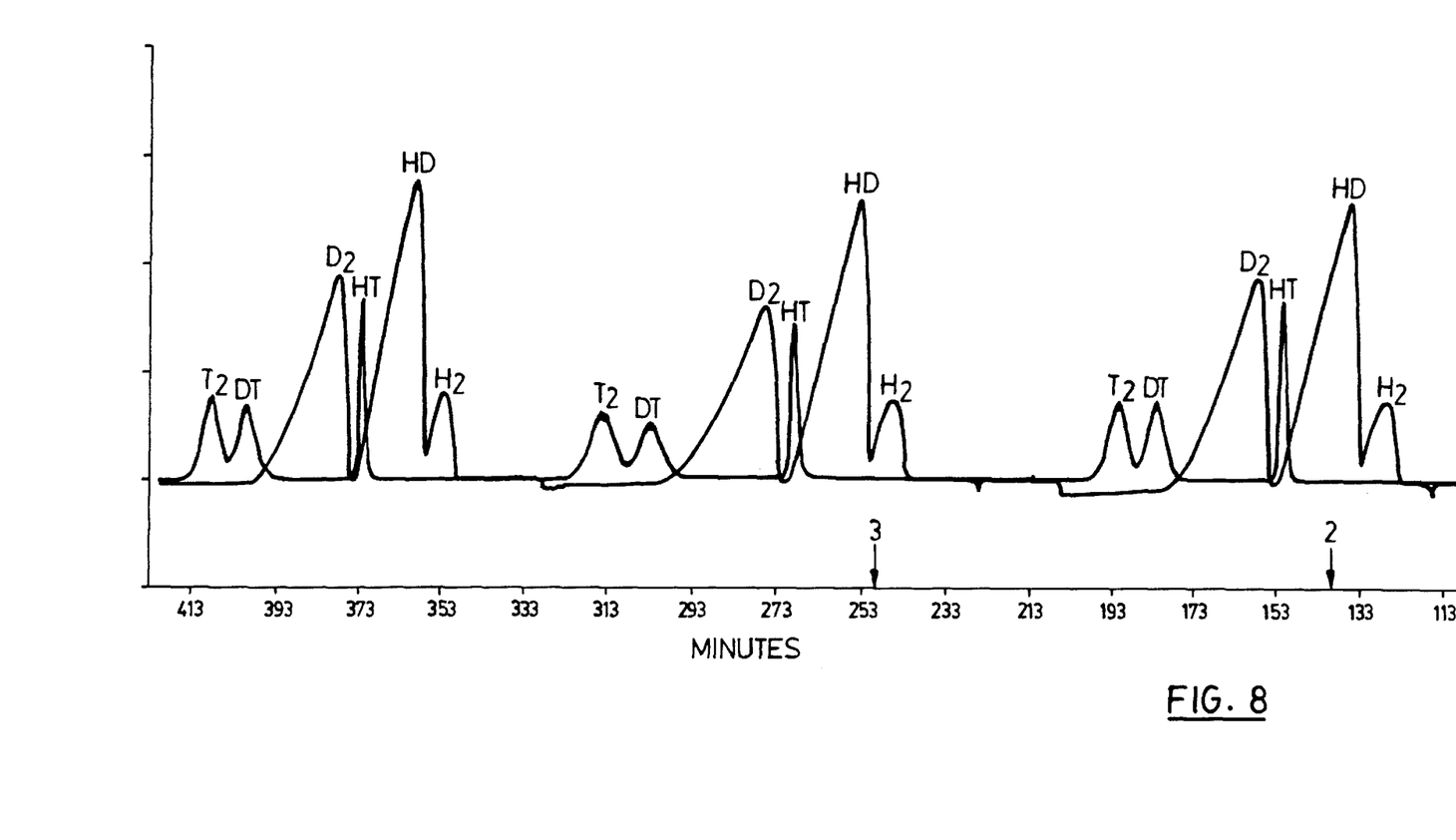

As seen from the chromatogram of FIG. 8, $H_2$ began eluting from the second column 10 after about 2 hrs. At about 140 min. the first column 30 was isolated from the elution stream, reimmersed in liquid nitrogen and a second mixture of 1.0 l (at 0° C., 1 atm.) containing the six hydrogen isotope species was loaded onto the first column 30 using the vacuum feed mode (see arrow 2, FIG. 8). Elution of the two columns in series proceeded as before, and the liquid nitrogen container was again gradually retracted over about a 30 minute period.

At about 250 min., as $H_2$ from this second mixture eluted from the second column 10, the first column 30 was again isolated from the elution stream, reimmersed in liquid nitrogen and a third mixture of 1.1 l (at 0° C., 1 atm.) containing the six hydrogen isotope species was loaded onto the first column 30 using the vacuum feed mode (see arrow 3, FIG. 8). Elution of the two columns in series then proceeded as before, and the liquid nitrogen container was again gradually retracted over about a 30 minute period. The chromatogram of the total separation of the three batches is shown in FIG. 8.

As seen from the foregoing examples, large amounts of similar species can be separated in accordance with the invention using surprisingly small columns. The skilled person will appreciate the general applicability of the invention from the foregoing description and examples of its exceptional power.

We claim:

1. A gas chromatographic method, comprising:
   loading a mixture onto a column packed with a stationary phase wherein mixture components of interest have different affinities for the stationary phase, the column is maintained at an elution temperature profile wherein the temperature increases along the column length from the inlet to the outlet of the column;
   flowing the mixture through the column to effect at least a partial separation of the mixture components; and
   recovering the separated or partially separated components from the outlet of the column.

2. A gas chromatographic method, comprising:
   loading a mixture onto a first column packed with a stationary phase wherein mixture components of interest have different affinities for the stationary phase, the column is maintained at an elution temperature profile wherein the temperature increases along the column length from the inlet to the outlet;
   flowing the mixture through the first column to effect at least a partial separation of the mixture components;
   flowing the effluent from the first column through a second column packed with a stationary phase wherein mixture components of interest have different affinities for the stationary phase, the column is maintained at a temperature profile wherein the temperature decreases along the column length from the inlet to the outlet; and
   recovering the separated components of the mixture from the outlet of the second column.

3. A chromatographic method as claimed in claim 2, wherein a mixture of hydrogen isotopes are separated using molecular sieves as a column stationary phase and the columns are maintained in the temperature ranges of −130° C. to −175° C.

4. A chromatographic method as claimed in claim 3, wherein the column diameters are in the range of 10–15 mm, and column lengths are 4.5–5.5 m.

5. A gas chromatographic method, comprising:
   loading a mixture onto a column packed with a stationary phase wherein mixture components of interest have different affinities for the stationary phase, the column is then provided with a variable elution temperature profile decreasing along the column length from the inlet to the outlet of the column;
   flowing the mixture through the column to effect at least a partial separation of the mixture components; and
   recovering the separated or partially separated components from the outlet of the column.

6. A chromatographic method as claimed in claim 5, further comprising flowing the effluent from the variable elution temperature profile first chromatography column through a second chromatography column maintained at a temperature profile wherein the temperature increases along the length of the second column from the inlet to the outlet; and recovering the separated components of the mixture from the outlet of the second column.

7. A chromatographic method as claimed in claim 6, wherein a mixture of hydrogen isotopes are separated using molecular sieves as a column stationary phase, the temperature profile of the variable elution temperature profile first column varies within the range 0° C. to −196° C. and the temperature profile in second column is fixed in the range of −130° C. to −175° C.

8. A chromatographic method as claimed in claim 5, further comprising flowing the effluent from the variable elution temperature profile first chromatography column through a second chromatography column maintained at an elution temperature profile wherein the temperature increases along the length of the second column from the inlet to the outlet; flowing the mixture through the second column to effect at least a partial separation of the mixture components; flowing the effluent from the second column through a third chromatography column maintained at a temperature profile wherein the temperature decreases along the length of the third column from the inlet to the outlet; and recovering the separated components of the mixture from the outlet of the third column.

9. A chromatographic method as claimed in claim 8, wherein a mixture of hydrogen isotopes are separated using molecular sieves as a column stationary phase, the temperature profile in the first column varies within the range 0° C. to −196° C., and the temperature profiles in the second and third columns is fixed in the range of −130° C. to −175° C.

* * * * *